United States Patent
Mian et al.

(10) Patent No.: US 8,649,932 B2
(45) Date of Patent: Feb. 11, 2014

(54) VEHICLE EVALUATION USING INFRARED DATA

(71) Applicant: International Electronic Machines Corporation, Troy, NY (US)

(72) Inventors: Zahid F. Mian, Loudonville, NY (US); Robert W. Foss, Cohoes, NY (US)

(73) Assignee: International Electronic Machines Corp., Troy, NY (US)

( * ) Notice: Subject to any disclaimer, the term of this patent is extended or adjusted under 35 U.S.C. 154(b) by 0 days.

(21) Appl. No.: 13/911,613

(22) Filed: Jun. 6, 2013

(65) Prior Publication Data

US 2013/0268155 A1 Oct. 10, 2013

Related U.S. Application Data

(63) Continuation of application No. 11/748,714, filed on May 15, 2007, now Pat. No. 8,478,480.

(60) Provisional application No. 60/854,703, filed on Oct. 27, 2006.

(51) Int. Cl.
*G01M 17/10* (2006.01)

(52) U.S. Cl.
USPC .......... 701/33; 701/29.1; 701/29.3; 701/29.6; 701/31.4; 701/33.7; 701/33.8; 702/1; 702/33; 702/40; 348/148; 348/163; 250/316.1; 250/330; 250/332; 250/334

(58) Field of Classification Search
None
See application file for complete search history.

(56) References Cited

U.S. PATENT DOCUMENTS

| | | | |
|---|---|---|---|
| 2,999,151 A | 9/1961 | Rosett | |
| 3,596,519 A | 8/1971 | Blonder et al. | |
| 3,767,146 A | 10/1973 | Gallagher | |
| 3,812,343 A | 5/1974 | Gallagher et al. | |
| 4,068,811 A | 1/1978 | Caulier | |
| 4,313,583 A | 2/1982 | Bambara et al. | |
| 4,608,599 A | 8/1986 | Kaneko et al. | |
| 4,659,043 A | 4/1987 | Gallagher | |
| 4,679,068 A | 7/1987 | Lillquist et al. | |

(Continued)

FOREIGN PATENT DOCUMENTS

JP    2005351705    12/2005

OTHER PUBLICATIONS

Christiaen et al., "Evaluation of Infrared Brake Screening Technology: Final Report," U.S. Department of Transportation, Dec. 2000, 90 pages.

(Continued)

*Primary Examiner* — Jonathan M Dager
(74) *Attorney, Agent, or Firm* — LaBatt, LLC

(57) ABSTRACT

A solution for evaluating a vehicle using infrared data is provided. In particular, evaluation data for the vehicle is obtained, which includes infrared data for a plurality of sides of the vehicle as well as vehicle identification data for distinguishing the vehicle from another vehicle. The infrared data is processed to enhance a set of signal features. Additional non-infrared based data also can be obtained for evaluating the vehicle. The evaluation data is analyzed to determine whether one or more anomalies are present. The anomaly(ies) can be correlated with a possible problem with a component of the vehicle. Data on the anomaly, problem, and/or vehicle identification can be provided for use on another system, such as a remote inspection station, maintenance system, and/or the like.

20 Claims, 9 Drawing Sheets

(56) References Cited

U.S. PATENT DOCUMENTS

| | | | |
|---|---|---|---|
| 4,751,571 A | 6/1988 | Lillquist | |
| 4,820,057 A | 4/1989 | Berndt | |
| 4,878,761 A | 11/1989 | Duhrkoop | |
| 4,977,586 A | 12/1990 | Curry | |
| 5,060,890 A | 10/1991 | Utterback et al. | |
| 5,100,243 A | 3/1992 | Grosskopf et al. | |
| 5,133,605 A | 7/1992 | Nakamura | |
| 5,201,483 A | 4/1993 | Sutnar et al. | |
| 5,331,311 A * | 7/1994 | Doctor | 340/463 |
| 5,381,700 A | 1/1995 | Grosskopf, Jr. | |
| 5,397,900 A | 3/1995 | Wetzler | |
| 5,448,072 A | 9/1995 | Gallagher | |
| 5,449,910 A * | 9/1995 | Wood et al. | 250/338.1 |
| 5,478,151 A | 12/1995 | Duhrkoop | |
| 5,583,765 A | 12/1996 | Kleehammer | |
| 5,636,026 A * | 6/1997 | Mian et al. | 356/602 |
| 5,660,470 A | 8/1997 | Mench | |
| 5,677,533 A * | 10/1997 | Yaktine et al. | 250/342 |
| 5,730,526 A * | 3/1998 | Davis et al. | 374/45 |
| 5,743,645 A | 4/1998 | Jaynes | |
| 5,936,737 A * | 8/1999 | Naumann | 356/613 |
| 5,942,753 A * | 8/1999 | Dell | 250/338.1 |
| 5,959,365 A * | 9/1999 | Mantini et al. | 307/10.1 |
| 6,353,223 B1 * | 3/2002 | Ookawa | 250/330 |
| 6,386,038 B1 * | 5/2002 | Lewis et al. | 73/587 |
| 6,442,457 B1 | 8/2002 | Jones et al. | |
| 6,476,722 B1 * | 11/2002 | Bidone | 340/584 |
| 6,595,684 B1 | 7/2003 | Casagrande et al. | |
| 6,637,703 B2 * | 10/2003 | Matheson et al. | 246/124 |
| 6,695,472 B1 | 2/2004 | Nayer | |
| 6,748,797 B2 | 6/2004 | Breed et al. | |
| 6,768,551 B2 * | 7/2004 | Mian et al. | 356/446 |
| 6,813,581 B1 * | 11/2004 | Snyder | 702/130 |
| 6,862,936 B2 * | 3/2005 | Kenderian et al. | 73/636 |
| 6,872,945 B2 * | 3/2005 | Bartonek | 250/339.04 |
| 6,883,962 B2 | 4/2005 | Kurata | |
| 6,909,514 B2 * | 6/2005 | Nayebi | 356/601 |
| 6,911,914 B2 * | 6/2005 | Mathews et al. | 340/682 |
| 6,982,653 B2 | 1/2006 | Voeller et al. | |
| 6,985,803 B2 * | 1/2006 | Abdel-Malek et al. | 701/31.5 |
| 7,103,460 B1 | 9/2006 | Breed | |
| 7,132,653 B2 * | 11/2006 | Faubion | 250/330 |
| 7,254,482 B2 | 8/2007 | Kawasaki et al. | |
| 7,280,898 B2 | 10/2007 | Lesesky et al. | |
| 7,349,007 B2 | 3/2008 | Millar | |
| 7,507,965 B2 * | 3/2009 | Lane et al. | 250/339.05 |
| 7,564,569 B2 * | 7/2009 | Mian et al. | 356/601 |
| 7,602,506 B2 * | 10/2009 | Hoffmann et al. | 356/602 |
| 7,715,026 B2 * | 5/2010 | Nayebi | 356/625 |
| 8,006,559 B2 | 8/2011 | Mian et al. | |
| 8,478,480 B2 | 7/2013 | Mian et al. | |
| 2002/0097321 A1 * | 7/2002 | McBride | 348/148 |
| 2003/0214395 A1 * | 11/2003 | Flowerday et al. | 340/445 |
| 2005/0021283 A1 * | 1/2005 | Brinton et al. | 702/150 |
| 2005/0132587 A1 * | 6/2005 | Larson et al. | 33/203.12 |
| 2005/0145794 A1 * | 7/2005 | Faubion | 250/330 |
| 2005/0258943 A1 * | 11/2005 | Mian et al. | 340/426.1 |
| 2005/0259273 A1 * | 11/2005 | Mian et al. | 356/601 |
| 2005/0267707 A1 * | 12/2005 | Mian et al. | 702/122 |
| 2005/0270537 A1 * | 12/2005 | Mian et al. | 356/437 |
| 2006/0030985 A1 * | 2/2006 | Lawida et al. | 701/35 |
| 2006/0033985 A1 * | 2/2006 | Mian | 359/366 |
| 2006/0043296 A1 * | 3/2006 | Mian et al. | 250/330 |
| 2006/0091310 A1 * | 5/2006 | Furry | 250/330 |
| 2006/0114531 A1 * | 6/2006 | Webb et al. | 359/15 |
| 2006/0131464 A1 * | 6/2006 | Hesser et al. | 246/169 D |
| 2006/0170768 A1 * | 8/2006 | Riley | 348/143 |
| 2006/0180760 A1 * | 8/2006 | Lane et al. | 250/339.05 |
| 2007/0030349 A1 * | 2/2007 | Riley | 348/143 |
| 2007/0040911 A1 * | 2/2007 | Riley | 348/148 |
| 2007/0064244 A1 * | 3/2007 | Mian et al. | 356/601 |
| 2007/0075192 A1 * | 4/2007 | Mian et al. | 246/1 R |
| 2007/0211145 A1 * | 9/2007 | Kilian et al. | 348/148 |
| 2008/0028846 A1 * | 2/2008 | Heath et al. | 73/146 |
| 2008/0143338 A1 * | 6/2008 | Sekine et al. | 324/503 |
| 2009/0018721 A1 | 1/2009 | Mian et al. | |
| 2009/0049936 A1 * | 2/2009 | Mian et al. | 73/865.8 |
| 2009/0055041 A1 * | 2/2009 | Mian et al. | 701/29 |
| 2009/0055043 A1 * | 2/2009 | Mian et al. | 701/29 |
| 2009/0208059 A1 | 8/2009 | Geva et al. | |
| 2009/0290757 A1 * | 11/2009 | Mian et al. | 382/104 |
| 2010/0076631 A1 | 3/2010 | Mian | |
| 2010/0100275 A1 * | 4/2010 | Mian et al. | 701/29 |
| 2010/0161255 A1 * | 6/2010 | Mian et al. | 702/56 |
| 2011/0024576 A1 * | 2/2011 | Kilian et al. | 246/169 A |

OTHER PUBLICATIONS

Dager, USPTO Office Action, U.S. Appl. No. 11/748,714, Notification Date Feb. 18, 2010, 19 pages.
Dager, USPTO Final Office Action, U.S. Appl. No. 11/748,714, Notification Date Jun. 14, 2010, 24 pages.
Dager, USPTO Office Action, U.S. Appl. No. 11/748,714, Notification Date Mar. 1, 2012, 10 pages.
Dager, USPTO Office Action, U.S. Appl. No. 11/748,714, Notification Date Jul. 30, 2012, 19 pages.
Dager, USPTO Final Office Action, U.S. Appl. No. 11/748,714, Notification Date Dec. 31, 2012, 13 pages.
Dager, USPTO Notice of Allowance, U.S. Appl. No. 11/748,714, Notification Date Apr. 12, 2013, 11 pages.
Freedman, USPTO Office Action, U.S. Appl. No. 12/603,958, Notification Date Mar. 12, 2012, 33 pages.
Freedman, USPTO Notice of Allowance, U.S. Appl. No. 12/603,958, Notification Date Aug. 16, 2012, 11 pages.

* cited by examiner

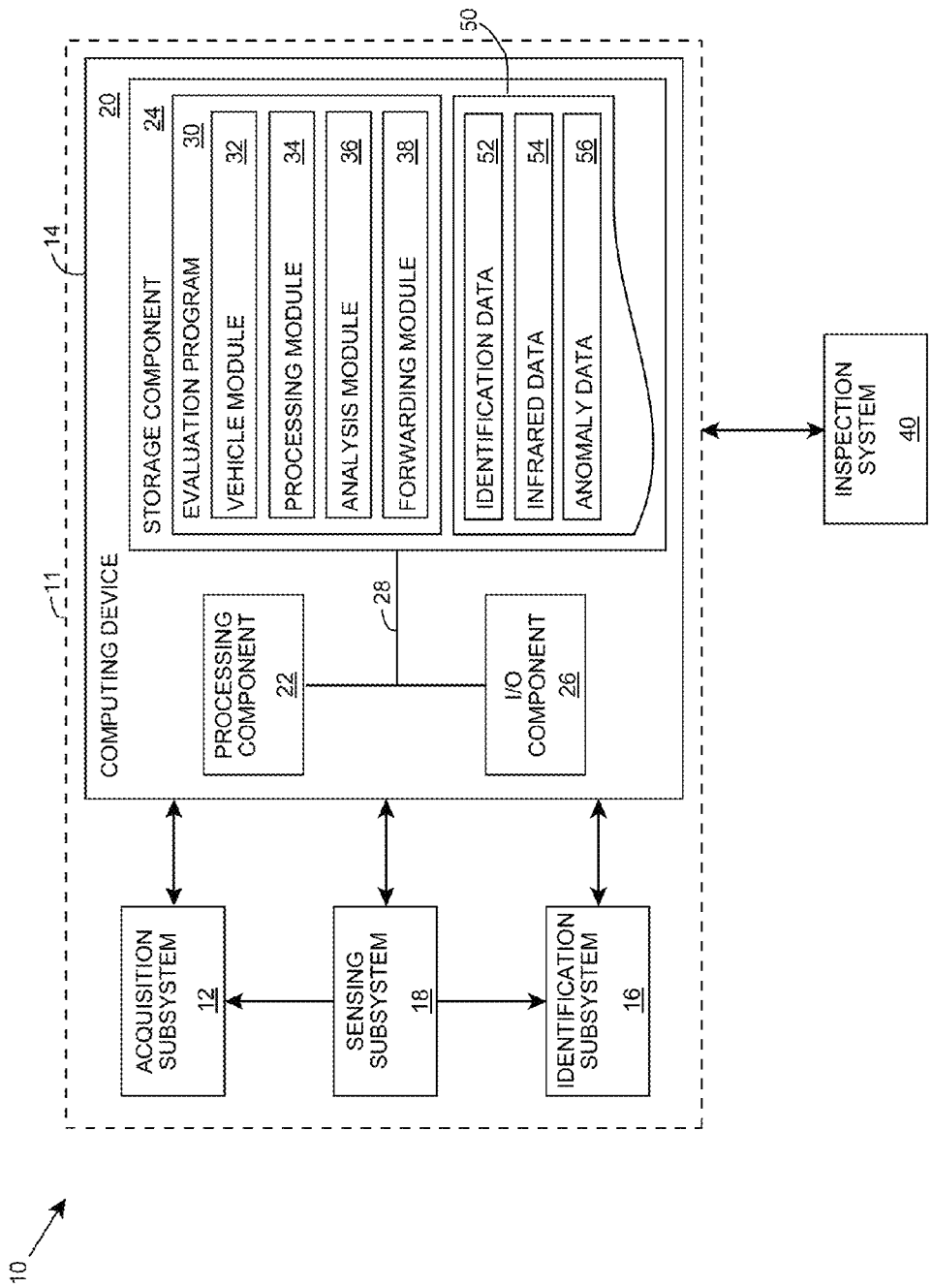

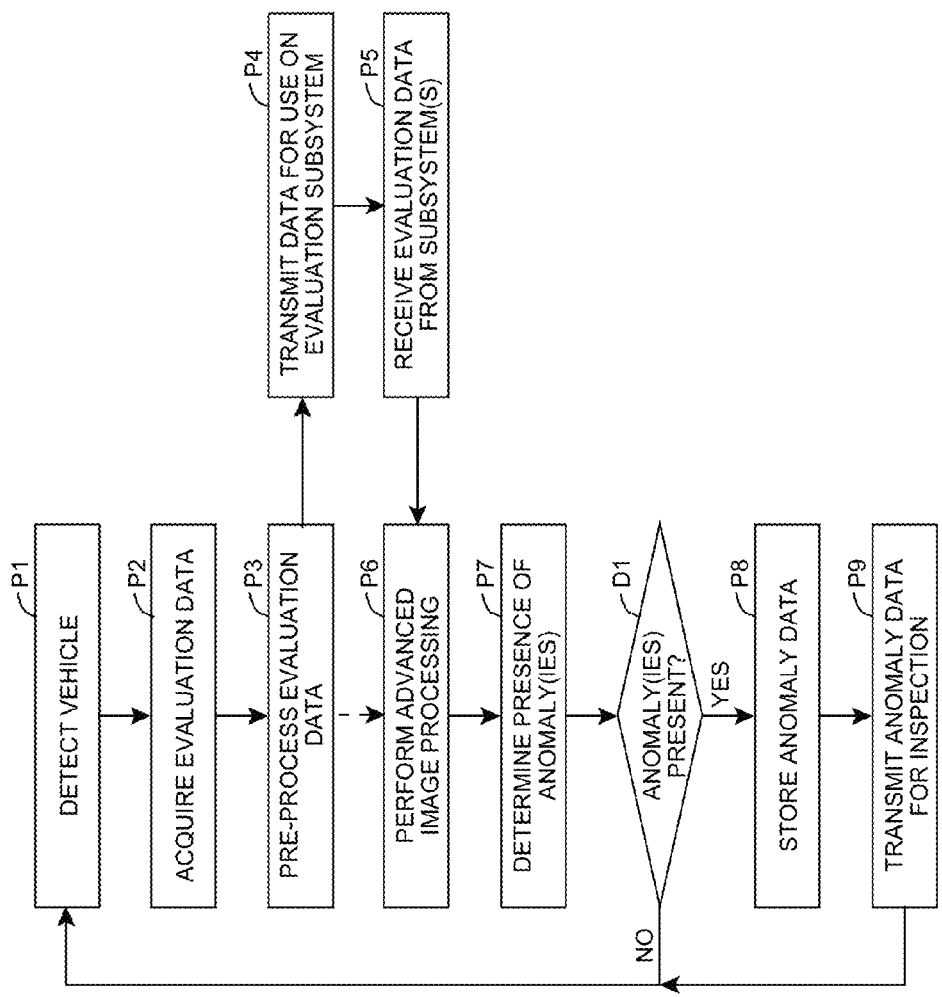

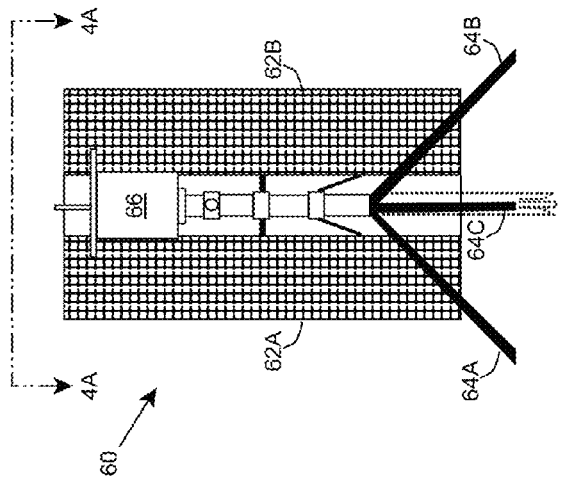
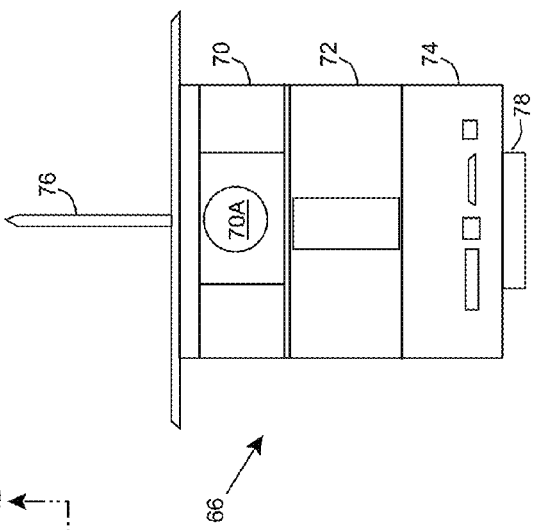
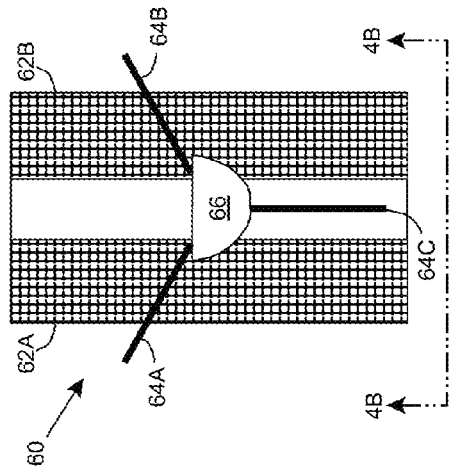

VEHICLE EVALUATION USING INFRARED DATA

REFERENCE TO PRIOR APPLICATIONS

The current application is a continuation of U.S. patent application Ser. No. 11/748,714, entitled "Vehicle Evaluation Using Infrared Data," which was filed on 15 May 2007, and which claims the benefit of U.S. Provisional Application No. 60/854,703, entitled "Multifunctional vehicle inspection system and device", which was filed on 27 Oct. 2006, both of which are hereby incorporated by reference.

GOVERNMENT LICENSE RIGHTS

The U.S. Government has a paid-up license in this invention and the right in limited circumstances to require the patent owner to license others on reasonable terms as provided for by the terms of Contract Number MC-06-RA-01-G-00000 awarded by the Federal Motor Carrier Safety Administration (FMCSA) of the U.S. Department of Transportation.

FIELD OF THE INVENTION

Aspects of the invention relate generally to vehicle evaluation, and more particularly, to a solution for evaluating a vehicle using infrared data.

BACKGROUND OF THE INVENTION

Vehicles, particularly commercial vehicles such as trucks, buses, and the like, transport millions of tons of cargo and millions of passengers to a variety of destinations worldwide. While the overwhelming majority of these trips are uneventful, a significant number of these trips experiences a problem due to a failure of a component of the vehicle itself. Such a problem can cause a delay and/or an accident, the latter of which may result in damage to the vehicle, its cargo, injured individual(s), loss of life, and/or the like.

To limit the unanticipated failure of a vehicle component, most vehicles, and all commercial vehicles, are generally required to undergo regular inspections. Further, additional inspections, particularly of commercial vehicles, often are carried out at random times and/or locations by members of state and/or federal enforcement organizations (e.g., state police, Department of Transportation, etc.). However, with a large number of vehicles involved in a random inspection, it is extremely difficult for an inspector to reliably select the vehicles most likely to experience a failure. Often, this is due to the limited resources and technologies available to the inspector and/or the implementation of the component. For example, electric and hydraulic brakes, unlike air brakes, cannot be readily visually evaluated by an inspector since they have no visible moving parts.

It is well known that brakes will heat up when used to slow a vehicle since the friction will dissipate the motion energy into heat. When a brake is not functioning properly, excessive or insufficient heat may be present in the braking area after the brakes have been used. Similarly, other components of a vehicle may show abnormal heat distribution as they approach failure. For example, improperly functioning bearings may result in increased friction, and therefore heat, between a wheel and an axle. Additionally, a failing tire may have increased heat in an area due to increased flexing and friction. A heat differential also can indicate other significant phenomena, such as leakage of cargo (e.g., from a tanker), leakage of exhaust, and/or the like.

Some inspection approaches use heat to determine if a vehicle brake component must be directly tested. For example, an inspector may place his/her hand near a vehicle's hydraulic or electric brake area to determine if it appears abnormally warmer than the surrounding air. However, this approach has a number of drawbacks including variations in inspectors and environmental conditions, variations in the amount of braking used (e.g., loaded versus unloaded truck), slow and invasive examination, which requires the truck to be stopped, and the like. Additionally, another approach uses thermal, or infrared, imaging to detect a defect in a vehicle brake component. In this approach, a human user evaluates a thermal image as a vehicle passes an imaging system set up adjacent to a road. However, this approach is limited in that, among other things, it requires a specially trained individual to evaluate the thermal images and/or operate the system, only a single side of the vehicle is imaged, it fails to address communications with an inspection site and/or logging data, and the like.

BRIEF SUMMARY OF THE INVENTION

Aspects of the invention provide a solution for evaluating a vehicle using infrared data. In particular, evaluation data for the vehicle is obtained, which includes infrared data for a plurality of sides of the vehicle as well as vehicle identification data for distinguishing the vehicle from another vehicle. The infrared data is processed to enhance a set of signal features. Additional non-infrared based data also can be obtained for evaluating the vehicle. The evaluation data is analyzed to determine whether one or more anomalies are present. The anomaly(ies) can be correlated with a possible problem with a component of the vehicle. Data on the anomaly, problem, and/or vehicle identification can be provided for use on another system, such as a remote inspection station, maintenance system, and/or the like.

A first aspect of the invention provides a method of evaluating a vehicle, the method comprising: obtaining evaluation data for the vehicle, the obtaining including: obtaining infrared data for a plurality of sides of the vehicle; processing the infrared data to enhance a signal feature; and obtaining vehicle identification data for distinguishing the vehicle from another vehicle; analyzing the infrared data to determine a presence of at least one anomaly; and providing a result of the analyzing and the vehicle identification data for use at a remote inspection station.

A second aspect of the invention provides a system for evaluating a vehicle, the system comprising: a system for obtaining evaluation data for the vehicle, the system for obtaining including: a system for obtaining infrared data for a plurality of sides of the vehicle; a system for processing the infrared data to enhance a signal feature; and a system for obtaining vehicle identification data for distinguishing the vehicle from another vehicle; a system for analyzing the infrared data to determine a presence of at least one anomaly; and a system for providing a result of the analyzing and the vehicle identification data for use at a remote inspection station.

A third aspect of the invention provides a system for evaluating a vehicle, the system comprising: a system for automatically detecting the vehicle; a system for obtaining evaluation data for the vehicle, the system for obtaining evaluation data including: a first infrared device on a first side of the vehicle; a second infrared device on a second side of the vehicle; and an identification device for obtaining vehicle identification data for distinguishing the vehicle from another vehicle; and a system for analyzing the evaluation data to determine a presence of at least one anomaly.

Other aspects of the invention provide methods, systems, program products, and methods of using and generating each, which include and/or implement some or all of the actions described herein. The illustrative aspects of the invention are designed to solve one or more of the problems herein described and/or one or more other problems not discussed.

BRIEF DESCRIPTION OF THE SEVERAL VIEWS OF THE DRAWINGS

These and other features of the invention will be more readily understood from the following detailed description of the various aspects of the invention taken in conjunction with the accompanying drawings that depict various embodiments of the invention.

FIG. 2 shows a more detailed view of the computer system of FIG. 1 according to an embodiment.

FIG. 3 shows an illustrative process for evaluating a vehicle according to an embodiment.

FIGS. 4A-C show an illustrative acquisition unit according to an embodiment.

It is noted that the drawings are not to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a solution for evaluating a vehicle using infrared data. In particular, evaluation data for the vehicle is obtained, which includes infrared data for a plurality of sides of the vehicle as well as vehicle identification data for distinguishing the vehicle from another vehicle. The infrared data is processed to enhance a set of signal features. Additional non-infrared based data also can be obtained for evaluating the vehicle. The evaluation data is analyzed to determine whether one or more anomalies are present. The anomaly(ies) can be correlated with a possible problem with a component of the vehicle. Data on the anomaly, problem, and/or vehicle identification can be provided for use on another system, such as a remote inspection station, maintenance system, and/or the like. As used herein, unless otherwise noted, the term "set" means one or more (i.e., at least one) and the phrase "any solution" means any now known or later developed solution.

Figure 1:
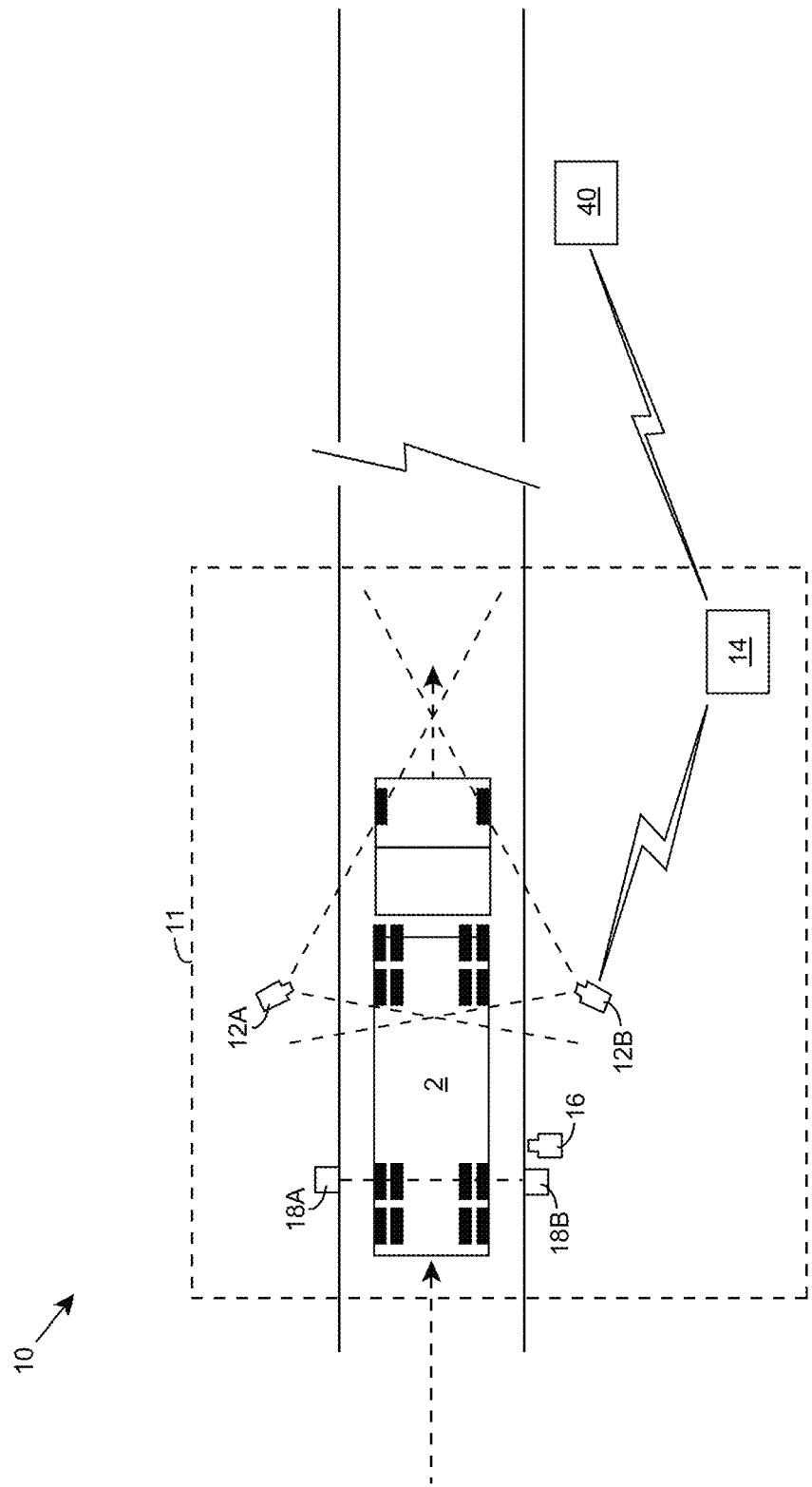
FIG. 1 shows an illustrative environment for evaluating a vehicle according to an embodiment.

Turning to the drawings, FIG. 1 shows an illustrative environment 10 for inspecting a vehicle 2 according to an embodiment. To this extent, environment 10 includes a computer system 11, which includes various computing devices 12A-B, 14, 16, and 18A-B that can perform the process described herein in order to evaluate vehicle 2. In particular, computer system 11 includes infrared devices 12A-B, an evaluation device 14, an identification device 16, and sensing devices 18A-B. During operation, sensing devices 18A-B can detect a presence of a vehicle 2, identification device 16 can obtain identification data for vehicle 2, and each infrared device 12A-B can obtain infrared data from a corresponding side of vehicle 2. Devices 12A-B, 16 can provide the raw data and/or preprocessed data for further processing on evaluation device 14.

Evaluation device 14 can perform advanced image processing on the infrared data and/or analyze the infrared data to determine whether one or more anomalies are present. As illustrated, computer system 11 is implemented in conjunction with an inspection system 40. To this extent, the evaluation of the infrared data can be performed as part of a pre-screening process for vehicles 2 being inspected. In this case, evaluation device 14 can communicate the results of the pre-screening of each vehicle 2 to inspection system 40, which is utilized in performing the inspection. Inspection system 40 can comprise any type of inspection system now known or later developed. Based on the result for vehicle 2, an inspector can adjust one or more aspects of the inspection (e.g., perform a more/less thorough inspection of a braking system).

FIG. 2 shows a more detailed view of computer system 11 according to an embodiment. In general, computer system 11 includes various subsystems, which can be implemented on one or more devices. Regardless, evaluation subsystem 14 (e.g., evaluation device 14 in FIG. 1) can communicate with acquisition subsystem 12 (e.g., one or more of infrared devices 12A-B in FIG. 1), sensing subsystem 18 (e.g., one or more of sensing devices 18A-B in FIG. 1), and/or identification subsystem 16 (e.g., identification device 16 in FIG. 1). In an embodiment, sensing subsystem 18 sends a notification to evaluation subsystem 14 when a vehicle 2 is detected, and evaluation subsystem 14 sends a notification to acquisition subsystem 12 and/or identification subsystem 16 to instruct subsystems 12, 16 to capture data on vehicle 2. Further, sensing subsystem 18 can send the notification directly to acquisition subsystem 12 and/or identification subsystem 16, as illustrated.

In any event, evaluation subsystem 14 is shown implemented as a computing device 20 that comprises an evaluation program 30, which makes computing device 20 operable to evaluate vehicle(s) 2 (FIG. 1) by performing the process described herein. Computing device 20 is shown including a processing component 22 (e.g., one or more processors), a storage component 24 (e.g., a storage hierarchy), an input/output (I/O) component 26 (e.g., one or more I/O interfaces and/or devices), and a communications pathway 28. In general, processing component 22 executes program code, such as evaluation program 30, which is at least partially stored in storage component 24. While executing program code, processing component 22 can read and/or write data to/from storage component 24 and/or I/O component 26. Pathway 28 provides a communications link between each of the components in computing device 20, while I/O component 26 provides a communications link between a user and computing device 20. To this extent, I/O component 26 can comprise one or more human I/O devices, which enable a human user to interact with computing device 20 and/or one or more communications devices to enable a system user, e.g., inspection system 40, to communicate with computing device 20 using any type of communications link.

Regardless, computing device 20 can comprise any general purpose computing article of manufacture capable of executing program code installed thereon. However, it is understood that computing device 20 and evaluation program 30 are only representative of various possible equivalent computing devices that may perform the process described herein. To this extent, in other embodiments, the functionality provided by computing device 20 and evaluation program 30 can be implemented by a computing article of manufacture that includes any combination of general and/or specific purpose hardware and/or program code. In each embodiment, the program code and hardware can be created using standard programming and engineering techniques, respectively.

Similarly, computer system 11 is only illustrative of various types of computer systems for implementing aspects of the invention. For example, in one embodiment, evaluation subsystem 14 comprises two or more computing devices that communicate over any type of communications link, such as a network, a shared memory, or the like, to perform the process described herein. Further, while performing the process described herein, one or more computing devices in computer system 11 can communicate with one or more other computing devices external to computer system 11 using any type of communications link. In any event, a communications link can comprise any combination of various types of wired and/or wireless links; comprise any combination of one or more types of networks; and/or utilize any combination of various types of transmission techniques and protocols.

As discussed herein, evaluation program 30 enables computing device 20 to evaluate a vehicle 2 (FIG. 1). To this extent, evaluation program 30 is shown including a vehicle module 32, a processing module 34, an analysis module 36, and a forwarding module 38. Operation of each of these modules is discussed further herein. However, it is understood that some of the various modules shown in FIG. 1 can be implemented independently, combined, and/or stored in memory of one or more separate computing devices that are included in computer system 11. Further, it is understood that some of the modules and/or functionality may not be implemented, or additional modules and/or functionality may be included as part of computer system 11. Still further, it is understood that the various subsystems 12, 14, 16, 18 can be implemented on any combination of one or more computing devices.

Regardless, aspects of the invention provide a solution for evaluating a vehicle, e.g., as part of a pre-inspection for a vehicle inspection location. FIG. 3 shows an illustrative process for evaluating a vehicle according to an embodiment, which can be implemented by computer system 11 (FIG. 2). Referring to FIGS. 1-3, in process P1, sensing subsystem 18 can automatically detect a presence of a vehicle 2. Sensing subsystem 18 can comprise any type of system capable of detecting a presence of vehicle 2 using any solution. For example, sensing subsystem 18 can comprise an electric eye, which includes a light sensor and/or light source (e.g., sensing devices 18A-B), a magnetic sensor, and/or the like.

In process P2, computer system 11 acquires evaluation data 50 for vehicle 2. Evaluation data 50 can include vehicle identification data 52 and infrared data 54. To this extent, identification subsystem 16 can obtain vehicle identification data 52 for distinguishing vehicle 2 from another vehicle, and acquisition subsystem 12 can obtain infrared data 54 for vehicle 2. In an embodiment, process P2 is performed automatically in response to a presence of vehicle 2 being detected in process P1. To this extent, identification subsystem 16 and acquisition subsystem 12 can be located in close proximity to sensing subsystem 18 so that a location and/or speed of vehicle 2 is known within a required accuracy. Further, computer system 11 can be located such that only vehicles 2 to be inspected are likely to be traveling and be detected. Still further, computer system 11 can be located such that it is highly probable that each vehicle 2 has recently applied its brakes, for example, at a rest area, a weigh station adjacent to a highway, at a bottom of a hill, and/or the like.

Identification subsystem 16 can acquire vehicle identification data 52 using any solution. To this extent, vehicle identification data 52 can comprise any type of data for distinguishing vehicle 2 from other vehicle(s) being evaluated. For example, identification subsystem 16 can include a radio frequency identification (RFID) tag reader, which obtains vehicle identification data 52 from an RFID tag on vehicle 2. Further, identification subsystem 16 can include an image/video-based identification system, which can obtain at least one visible image of vehicle 2. Still further, vehicle identification data 52 can include other data, such as a date/time stamp, a unique identifier (e.g., a serial number, a count), and/or the like. To this extent, vehicle module 32 can assign a unique identifier for the data for vehicle 2 upon its detection, which is subsequently provided to and used by other subsystems in computer system 11 to manage the corresponding evaluation data 50 and track vehicle 2 as it is evaluated and/or inspected.

Acquisition subsystem 12 can obtain infrared data 54 using any solution. For example, acquisition subsystem 12 can comprise a plurality of infrared-based imaging devices, which are located on multiple sides of vehicle 2. Each infrared-based imaging device can acquire a set of infrared images for a corresponding side of vehicle 2. In an embodiment, acquisition subsystem 12 includes two infrared devices 12A-B as shown in FIG. 1, each of which can acquire a set of infrared images as vehicle 2 passes through the corresponding fields of view. It is understood that the number, configuration, and fields of view of infrared devices 12A-B is only illustrative, and any number of infrared devices 12A-B can be used to obtain infrared image(s) for any side of vehicle 2, including the front, back, top, bottom, etc. Additionally, it is understood that an infrared image may include only a portion of vehicle 2.

Evaluation data 50 can include additional types of data, which can be acquired by acquisition subsystem 12 and/or another subsystem (not shown). For example, evaluation data 50 can include image data based on visible light, ultraviolet light, and/or the like and/or non-image data, such as radar data, X-ray data, radiation data, magnetic data, pressure data, spectrometric data, acoustic data, a weight of vehicle 2, and/or the like. To this extent, acquisition subsystem 12 can obtain any combination of various types of evaluation data 50 using any solution. For example, acquisition subsystem 12 can include a microphone array to acquire acoustic data for vehicle 2. Similarly, acquisition subsystem 12 can include contact-based (e.g., pressure) and/or non-contact-based (e.g., laser/diffuse light) sensor(s) for registering each wheel that passes for a vehicle 2. Still further, acquisition subsystem 12 can include a set of wireless receivers that can detect signals from sensor(s) or system(s), such as SAW-based RF tags, implemented on vehicle 2, and which monitor one or more operating characteristics of vehicle 2 (e.g., tire pressure, engine data, and/or the like).

In process P3, computer system 11 pre-processes evaluation data 50, such as vehicle identification data 52 and/or infrared data 54. For example, when identification subsystem 16 obtains a set of visible images for vehicle 2, identification subsystem 16 can pre-process the visible image(s) to extract, enhance, isolate, and/or the like, vehicle identification data 52 such as an image of a license plate, operating credentials (e.g., located on a side of the vehicle), and/or the like. Further, identification subsystem 16 can obtain vehicle identification data 52 that may not uniquely identify vehicle 2. For example, identification subsystem 16 can obtain a color of vehicle 2, a size/shape/type of vehicle 2 (e.g., truck tractor and/or trailer(s)), and/or the like. To this extent, identification subsystem 16 can ensure that vehicle 2 is a proper type of vehicle that is being inspected (e.g., not a passenger vehicle). Regardless, identification subsystem 16 can include the raw data (e.g., image(s)/video of vehicle 2) from which one or more identifying attributes of vehicle 2 is/are derived as vehicle identification data 52.

Additionally, acquisition subsystem 12 can pre-process some or all of evaluation data 50, such as infrared data 54. To this extent, each infrared device 12A-B can perform filtering, initial processing, and/or the like, on the infrared data using any solution. For example, infrared data corresponding to a critical portion of the image can be extracted. Additionally, an infrared image can be filtered to reduce incidental noise, glare, and/or the like. Further, an infrared device 12A-B can eliminate shadows, infrared or otherwise, from an image, e.g., using reflective symmetry detection, common movement, movement conforming to ground/field objects, and/or the like. Still further, when evaluation data 50 includes other types of data, acquisition subsystem 12 can perform noise reduction, signal amplification and smoothing, and/or the like, on evaluation data 50. The initial processing of evaluation data 50 also can include securing the data (e.g., watermarking, encrypting, and/or the like), compressing the data, and/or the like. In any event, acquisition subsystem 12 can store the pre-processed evaluation data 50 and/or the raw evaluation data 50 for each vehicle 2.

When computer system 11 includes multiple devices as illustrated in FIG. 1, in process P4, the devices that acquire evaluation data 50 can transmit the data for use on evaluation subsystem 14. For example, each infrared device 12A-B and identification device 16 can transmit infrared data 54 and vehicle identification data 52, respectively, for use on evaluation subsystem 14 using any solution. It is understood that the transmission can incorporate data security, data compression, and/or other transmission techniques known in the art. In an embodiment, the data is transmitted using a wireless communications solution. In this manner, computer system 11 can be readily set up on a temporary or permanent basis. Regardless, in process P5, evaluation subsystem 14 can receive evaluation data 50 from subsystems 12, 14 using any solution. Alternatively, one or more subsystems could be implemented on a single device, in which case processes P4-P5 may not be required.

In any event, in process P6, processing module 34 can process some or all of evaluation data 50. To this extent, processing module 32 can process image-based identification data 52 to extract one or more identifying features of vehicle 2 (e.g., a license plate number, operating credentials, and/or the like). Additionally, vehicle module 32 can match identification data, such as RFID tag information, a license plate number, operating credentials, and/or the like, with a known database of vehicles 2, e.g., in a state/national database, private fleet, and/or the like. Further, processing module 34 can perform advanced image processing on infrared data 54 to enhance (e.g., define, extract, identify, and/or the like) one or more signal features. For example, processing module 34 can subject infrared data 54 to one or more of segmentation, fusion between multiple images, feature detection, and/or the like. Additionally, when evaluation data 50 includes other types of data, processing module 34 can fuse different types of data in evaluation data 50. By using data fusion, processing module 34 can provide redundant evaluation data 50 that is more susceptible for accurate detection of various phenomena, and is less prone to false positive/negative readings.

In process P7, analysis module 36 can analyze evaluation data 50 to determine whether any anomalies may be present. To this extent, analysis module 36 can implement any combination of various decision-making solutions including a trained neural network, an expert system, template matching, a Markov Model, and/or the like. These decision-making solutions can examine some or all of evaluation data 50 to determine whether an anomaly is present. For example, a set of infrared images can be examined to determine whether one or more areas may exhibit heat that is outside of an expected range, e.g., either too cold or too hot. Analysis module 36 can analyze evaluation data 50 for the presence of various types of anomalies. Different types of evaluation data 50 may be more useful for determining different types of anomalies. For example, visible image data could be used to determine whether a leak, a loose hose, or the like, may be present on the vehicle, while ultraviolet image data could be used to identify the presence of excess strain or the like. Further, analysis module 36 can obtain anomaly information from one or more external sources. For example, analysis module 36 can provide a license plate, operating credentials, and/or the like, for comparison with a law enforcement database, maintenance history database, and/or the like. In this case, analysis module 36 can receive a response that indicates whether an anomaly may be present due to operation of the vehicle itself (e.g., stolen vehicle, suspended license, past due maintenance, and/or the like).

In decision D1, analysis module 36 can determine whether one or more anomalies are present. If so, in process P8, analysis module 36 can store anomaly data 56 for the vehicle. Anomaly data 56 can include information on the anomaly(ies) located in evaluation data 50. Further, anomaly data 56 can include one or more recommended actions as a result of the anomaly(ies). For example, anomaly data 56 can include a recommended type of inspection and/or area of inspection. When computer system 11 is implemented as a preliminary evaluation system (e.g., a pre-inspection system), in process P9, forwarding module 38 can transmit some or all of evaluation data 50, including anomaly data 56, for use by a primary evaluation system, such as inspection system 40, for temporary or permanent storage, and/or the like.

It is understood that the process is only illustrative of various processes that can be implemented. For example, forwarding module 38 can provide a result of the analysis together with vehicle identification data 52 for use by a remote, primary evaluation system, such as inspection system 40, for every vehicle, regardless of whether any anomaly(ies) were detected. Further, vehicle module 32 can manage all evaluation data 50 for one or more vehicles using any solution. To this extent, vehicle module 32 can store evaluation data 50 using any solution (e.g., one or more files, records in a database, and/or the like). Further, vehicle module 32 can manage an interface such as a user interface, application program interface (API), and/or the like, which enables a user to perform one or more operations on evaluation data 50. Still further, vehicle module 32 can automatically perform maintenance, such as purging evaluation data 50 that is no longer required, using any solution.

As described herein, an embodiment of acquisition subsystem 12 utilizes acquisition devices, such as infrared devices 12A-B, which are portable and can be readily deployed and/or removed. To this extent, FIGS. 4A-C show an illustrative acquisition unit 60 according to an embodiment. As illustrated in FIGS. 4A-B, acquisition unit 60 includes a power unit, which can include solar panels 62A-B, a support structure, which can include foldable legs 64A-C, and a sensor head 66. It is understood that solar panels 62A-B are only an illustrative solution for generating power for acquisition unit 60, and other solutions, including a power unit that does not include independent power generation (e.g., only a battery), can be utilized. Similarly, it is understood that foldable legs 64A-C are only illustrative, and the support structure can be implemented using any solution.

FIG. 4C shows a more detailed view of sensor head 66 according to an embodiment. Sensor head 66 includes an acquisition bay 70, an electronics bay 72, and an interface bay 74. Each bay 70, 72, 74 can include one or more components that implement various functions. For example, acquisition bay 70 can include a set of data acquisition devices, such as an infrared device 70A. Electronics bay 72 can include a set of components for data processing and storage, wireless communications, power supply and distribution components, and/or the like. Additionally, interface bay 74 can include one or more I/O interface ports (e.g., Ethernet, USB, Firewire, and/or the like), one or more I/O interface devices (e.g., display, keypad, and/or the like), a power interface (e.g., for a rechargeable battery), and/or the like. Further, sensor head 66 can include an antenna 76 for sending and/or receiving data via a wireless communications system, and a mounting collar 78 for permanently or temporarily mounting sensor head 66 to a permanent or portable support structure.

Acquisition bay 70 can include any type of data acquisition device(s) for acquiring a particular type of evaluation data 50 (FIG. 2). To this extent, infrared device 70A can comprise any type of infrared imaging device. For example, infrared device 70A can detect infrared radiation using an un-cooled microbolometer, an un-cooled line-scan camera, lower-resolution infrared imaging system, and/or the like. These types of infrared devices require less power than devices that utilize a cooled infrared sensor, which also can be implemented when sufficient power is not an issue (e.g., a permanent emplacement). When a line-scan camera is utilized, processing module 34 (FIG. 2) can combine the scanned infrared data with information on the vehicle's speed to produce an accurate scaled image from the successive slices scanned as the vehicle passed. Additionally, infrared device 70A can comprise: a near-infrared (NIR) imaging device, which is best when an anomaly is indicated by a several hundred degrees temperature difference; a medium-wave infrared (MWIR) imaging device, which can penetrate fog and very humid air; or a long-wave infrared (LWIR) imaging device. Moreover, infrared device 70A can comprise an imaging device that combines a lower-resolution infrared image with a higher-resolution visible light image to provide a fused infrared and visible light-based image.

Further, infrared device 70A could comprise a fixed imaging unit or a scanning sensor unit, such as a pan-tilt-zoom imaging device. In the latter case, infrared device 70A can be controlled by acquisition subsystem 12 (FIG. 2) and can scan key locations on vehicle 2 (FIG. 1). As a result, infrared device 70A can acquire zoomed, higher resolution images of the key locations for subsequent analysis by the remainder of computer system 11 (FIG. 2). Additionally, with a zoom capability, infrared device 70A can be placed at a greater distance from vehicle 2 and still obtain high resolution image data for vehicle 2.

An image acquired by infrared device 70A can be blurred when the image is captured before the microbolometers deplete their existing charge from acquiring a previous image. Infrared device 70A and/or electronics bay 72 can include one or more components to address this problem using any solution. For example, infrared device 70A can include an external physical shutter that shuts down the frame for a sufficient period of time to clear the infrared device 70A. Further, infrared device 70A can incorporate a wide field of view to avoid a large shift in the image from frame to frame. Still further, electronics bay 72 can process the image(s) using an image deblurring algorithm, or the like. In this case, information on the speed of vehicle 2 (FIG. 1) may be obtained (e.g., using a radar, visible-light movement analysis, and/or the like) and utilized by the algorithm. Still further, infrared device 70A can incorporate a lower time constant microbolometer, a cooled imager, and/or the like.

Infrared device 70A and/or electronics bay 72 also can incorporate one or more features for helping to ensure accurate infrared images. For example, infrared device 70A and/or electronics bay 72 can compensate for infrared drift offset. In particular, during use, the response to infrared radiation of pixels in infrared device 70A can shift slightly in unpredictable patterns. As a result, infrared device 70A can include a shutter-based recalibration, in which a shutter closes off the camera and the pixel offsets can be recalibrated to a temperature of the shutter. Frequently, the shutter-based recalibration is triggered periodically. In an embodiment, infrared device 70A and/or electronics bay 72 can trigger recalibration to occur frequently when a vehicle is not present so that infrared device 70A will have been recently recalibrated when a new vehicle is present. Additionally, infrared device 70A can include a "cold shield" that surrounds the infrared sensors and prevents any infrared interference resulting from heat radiating from one or more components in acquisition unit 60.

Sensor head 66 can be designed to operate in various weather conditions and withstand frequent movement. In particular, sensor head 66 can include a rugged construction, and include various solutions for protecting the operating components from rain, snow, and/or the like. Moreover, sensor head 66 can include various ancillary systems to ensure proper operation of the various components therein. To this extent, sensor head 66 can include environmental/system monitoring components, self-cleaning components, and/or the like.

Regardless, it is understood that sensor head 66 is only illustrative. For example, sensor head 66 could be implemented as a handheld device, which can be pointed at a vehicle 2 (FIG. 1) and acquire and process the relevant evaluation data 50 (FIG. 2). Further, in another embodiment, sensor head 66 and/or acquisition unit 60 includes some or all of the components for sensing subsystem 18 (FIG. 2) and/or identification subsystem 16 (FIG. 2). To this extent, sensing subsystem 18 could comprise a "radar gun", which can detect vehicle 2 at a sufficient range to prepare the other components for operation. Additionally, identification subsystem 16 could comprise a visible imaging device or the like, and the image(s) can be utilized by both identification subsystem 18 and acquisition subsystem 12.

Returning to FIGS. 1 and 2, acquisition subsystem 12 may include two or more acquisition units 60 (FIG. 4A) that are located on a plurality of sides of vehicle 2. For example, each infrared device 12A-B can be located on a corresponding acquisition unit 60. Similarly, sensing subsystem 18 and/or identification subsystem 16 can include one or more units that are configured similarly to acquisition unit 60, but include the appropriate sensing devices and processing capabilities to implement the corresponding functions for the respective subsystems 16, 18.

Figure 5A:
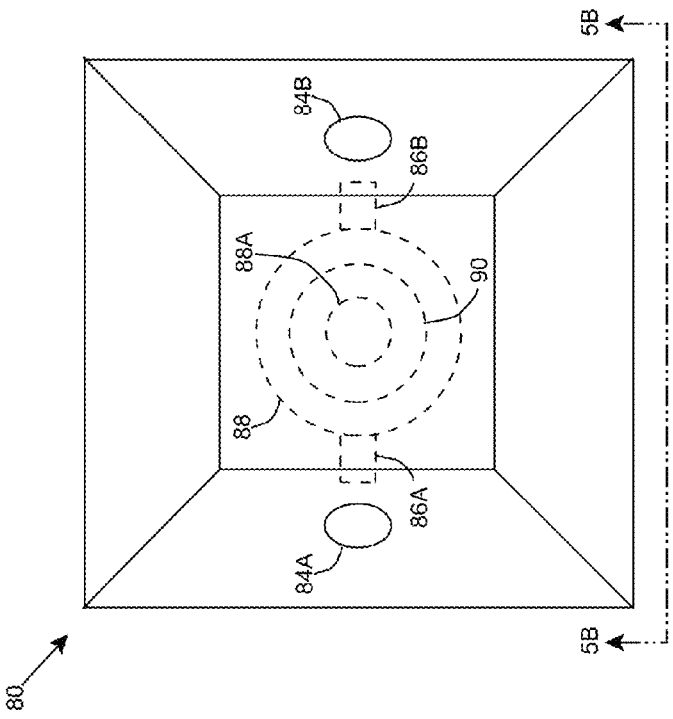
FIGS. 5A-C show another illustrative acquisition unit according to an embodiment.
Figure 5C:
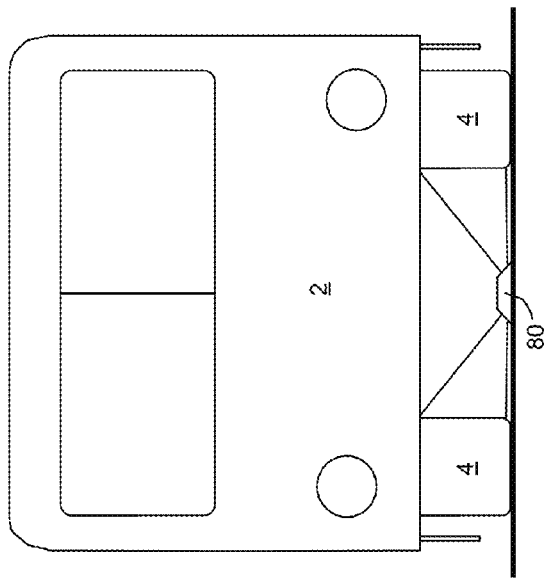
Figure 5B:
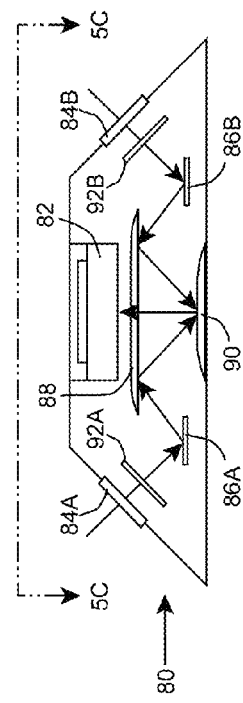

However, this is only illustrative, and acquisition subsystem 12, identification subsystem 16, and/or sensing subsystem 18 can include an acquisition unit in an alternative location. For example, FIGS. 5A-C show another illustrative acquisition unit 80 according to an embodiment. In particular, as shown in FIG. 5A, acquisition unit 80 is located in a path of vehicle 2 such that vehicle 2 will pass over acquisition unit 80. In this case, acquisition unit 80 can acquire evaluation data 50 (FIG. 2) from an interior side of vehicle 2. To this extent, acquisition unit 80 can acquire evaluation data 50 for an interior side of one or more wheels 4 (as shown). Further, acquisition unit 80 can acquire evaluation data 50 for an undercarriage of vehicle 2. Still further, as vehicle 2 is approaching and/or leaving the location of acquisition unit 80, acquisition unit 80 can acquire evaluation data 50 for a front and/or back of vehicle 2. Acquisition unit 80 can be permanently or temporarily placed at a location using any solution.

Acquisition unit 80 can include similar components as shown and described with respect to sensor head 66 (FIG. 4C). To this extent, acquisition unit 80 can include an imaging device, such as an infrared device and/or visible imaging device, for each side of vehicle 2 to be imaged, data processing, storage, interface, and communications components, a power source, and/or the like. In an embodiment, acquisition unit 80 includes a single imaging device for a plurality of sides of vehicle 2 to be imaged. For example, as shown in FIGS. 5B-C, acquisition unit 80 can include a single imaging device 82 (e.g., an infrared device, shown only in FIG. 5B for clarity) that images light (e.g., infrared light) that passes through both windows/lenses 84A-B. The light is then reflected from mirrors 86A-B onto a concave mirror 88 and then a convex mirror 90, which directs the light through a transparent portion 88A of concave mirror 88 and onto an imaging sensor of imaging device 82.

Acquisition unit 80 can include electronic shutters 92A-B (shown only in FIG. 5B for clarity) that alternatively block light passing through one of windows/lenses 84A-B to enable a clear acquisition of both fields of view. Electronic shutters 92A-B can operate at a speed commensurate with a frame rate of imaging device 82, thereby enabling each field of view to be imaged every nth frame (where n is the number of fields of view, two in this embodiment). Alternatively, imaging device 82 could image each field of view in a unique subdivision of its imaging area, thereby enabling simultaneous imaging of all fields of view.

Figure 6:
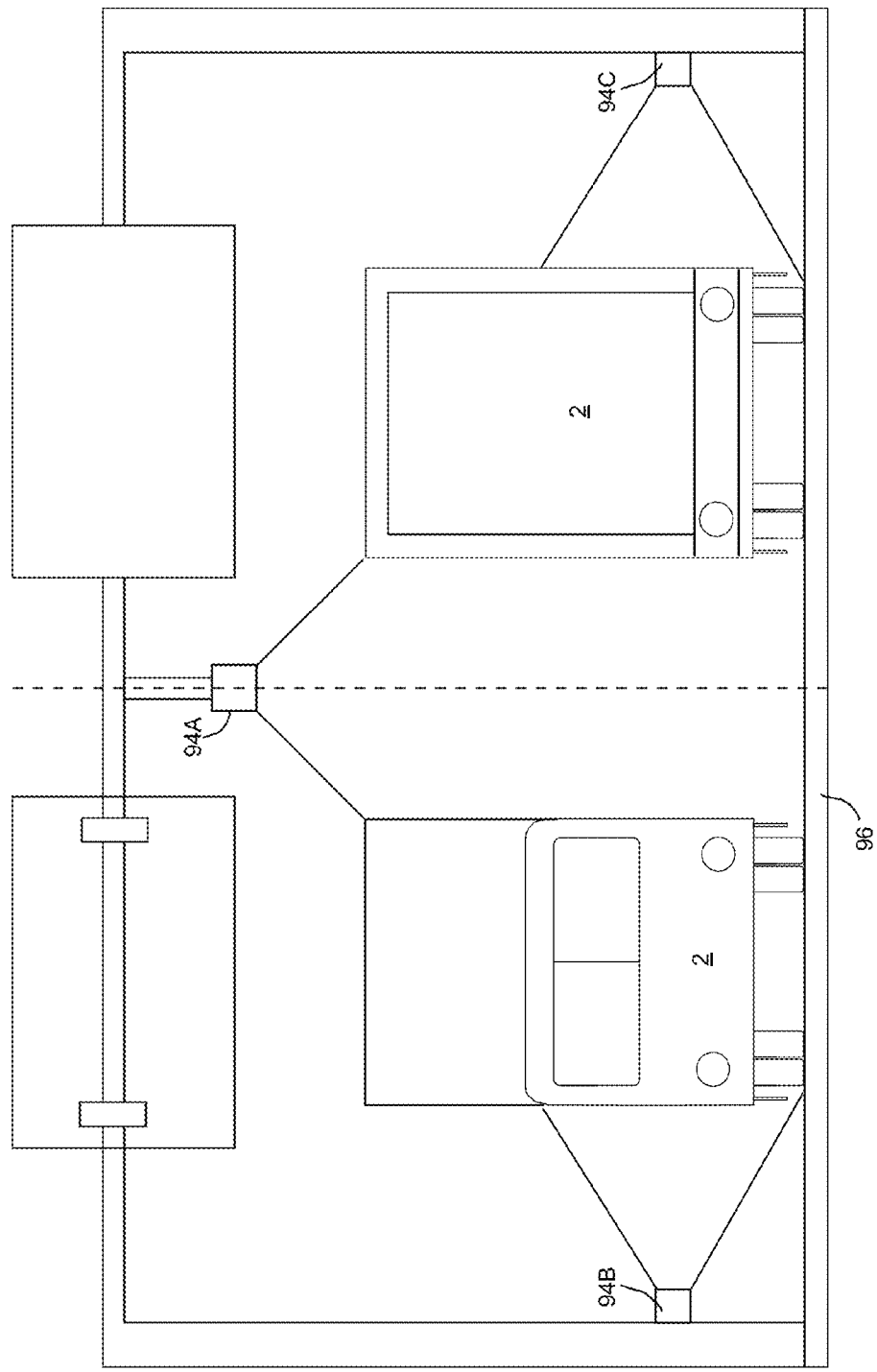
FIG. 6 shows an illustrative configuration of acquisition units according to an embodiment.

FIG. 6 shows an illustrative configuration of acquisition units 94A-C according to an embodiment. In this case, acquisition units 94A-C are configured for use in a high speed environment (e.g., a highway). As illustrated, acquisition units 94A-C are mounted to supports for road signage or the like. This can enable acquisition units 94A-C to acquire infrared data for vehicles 2 from various angles. Further, road 96 and/or other surfaces can include reflective material that can direct infrared data towards one or more acquisition units, such as acquisition unit 94A. Similarly, acquisition units 94A-C could be placed at other, lower speed locations, such as toll booths, or the like.

Returning to FIG. 2, depending on the type(s) of evaluation data 50 acquired and processed, analysis module 36 can detect any combination of various types of anomalies, and the corresponding flaws, that may be present on a vehicle 2 (FIG. 1). For example, analysis module 36 can detect acoustic anomalies, which can be used to identify a flawed (e.g., worn) bearing, malfunctioning engine, and/or the like. Further, some evaluation data 50 may identify an anomaly directly, such as a sufficiently high measurement of radiation data.

As discussed herein, analysis module 36 can use infrared data 54, such as one or more infrared images of vehicle 2, alone and/or in conjunction with other types of data to determine the presence of any anomalies in vehicle 2. To this extent, infrared data 54 that includes one or more areas that are hotter than normal can be used to detect defects such as: stuck brake, under-inflated/flat tire, leaking exhaust (heat in abnormal area), worn bearings, overheating engine compartment, cracked frame (causing additional flexing and therefore additional heat), overheating radiator, overheating cargo (e.g., chemicals or biologicals which may react with each other to create additional heat or even catch on fire—compost, rags filled with oil and other reactive solvents, sodium, etc.), and/or the like. Similarly, infrared data 54 that includes one or more areas that are cooler than normal can detect defects such as: failing brakes, non-operating brakes, loss of cooling in refrigerated area, and/or the like. Still further, analysis module 36 can process infrared data 54 to measure one or more attributes of a portion of vehicle 2, which analysis module 36 then uses to determine the presence of a defect. For example, analysis module 36 can thermally map tread depth for a wheel 4 (FIG. 5A) of vehicle 2 using infrared data 54, which analysis module 36 can compare to a standard to determine whether the tread depth is sufficient. Further, analysis module 36 can use infrared data 54 to identify unexpected voids within a cargo area (which would affect heat transmission through vehicle 2), which can then be flagged for a follow up inspection.

Figure 7:
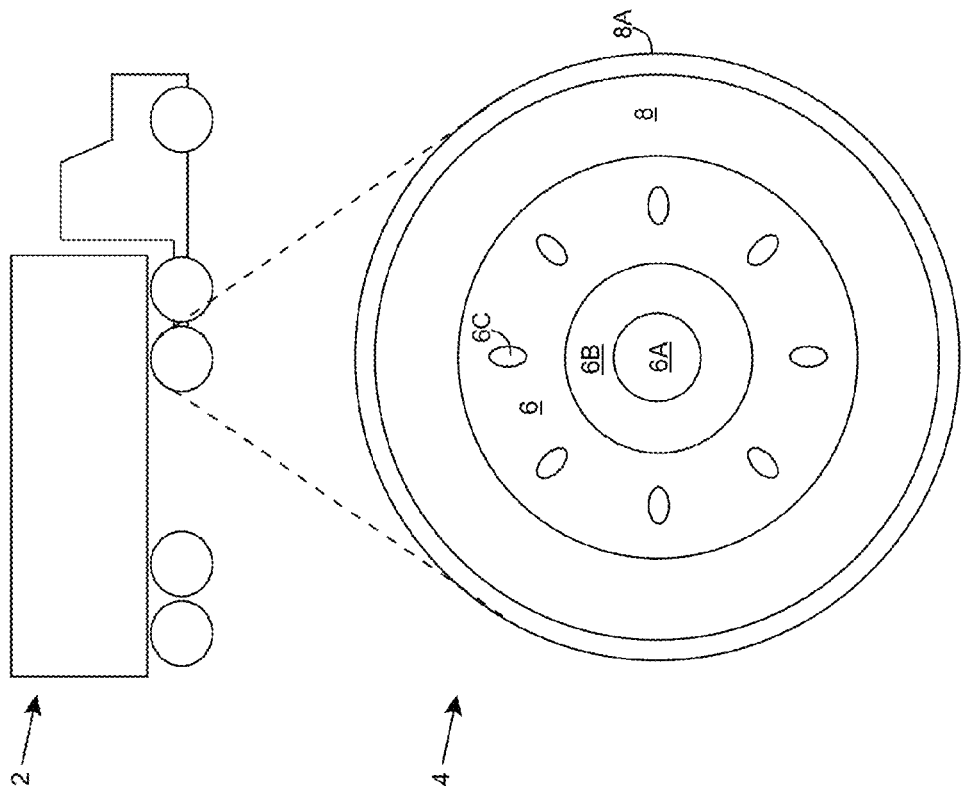
FIG. 7 shows an illustrative vehicle and vehicle wheel, which can be evaluated according to an embodiment.

Additional illustrative details are described with reference to the use of infrared image(s) to detect one or more anomalies with respect to the brakes, bearings, and/or wheels of a vehicle. To this extent, FIG. 7 shows an illustrative vehicle 2 and vehicle wheel 4, which can be evaluated according to an embodiment. In general, wheel 4 includes a wheel rim 6 and a tire 8. Wheel rim 6 is attached to a central axle 6A and includes a bearing area 6B (the bearings are internal in this area) and a plurality of holes, such as hole 6C, through which a brake drum can be viewed. Tire 8 is affixed to wheel rim 6 and contacts the road along a tread surface 8A.

When the brakes of vehicle 2 are applied, friction occurs at the brake drum and the corresponding heat dissipates through holes 6C. Similarly, a worn bearing will cause additional heat in bearing area 6B than that seen for a properly operating bearing. Further, abnormal heating of tread surface 8A will occur due to under-inflation, tread separation, and/or the like. In each case, analysis module 36 (FIG. 2) can examine infrared data 54 (FIG. 2) that includes a set of infrared images, each of which includes some or all of wheel 2 to determine the presence of one or more anomalies. In particular, analysis module 36 can examine the relevant portion(s) of wheel rim 6 and tread surface 8A to determine whether any brake, wheel, and/or bearing-related anomoly(ies) is/are present on vehicle 2.

Figure 8:
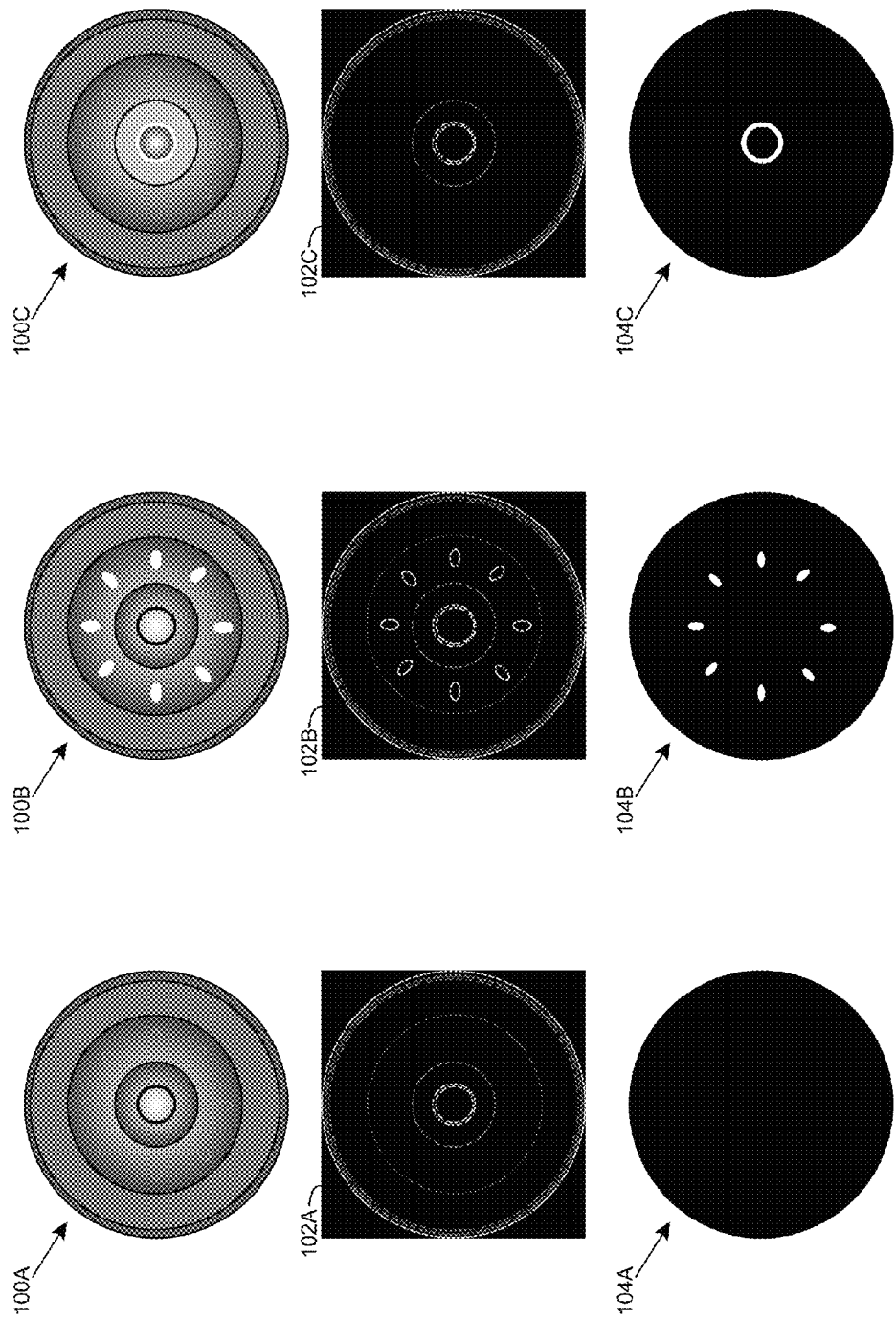
FIG. 8 shows an illustrative series of images of a wheel and the resulting infrared data after processing with two illustrative evaluation solutions according to an embodiment.

Analysis module 36 (FIG. 2) can process infrared image(s) of wheel 4 using any combination of one or more image processing algorithms. For example, FIG. 8 shows an illustrative series of images 100A-C of a wheel and the resulting infrared data after processing with two illustrative evaluation solutions according to an embodiment. In particular, analysis module 36 can generate infrared data 102A-C by processing the corresponding images 100A-C using an edge detection algorithm. The edge detection algorithm detects edges in an image by analyzing local brightness changes over short distances. Similarly, analysis module 36 can generate infrared data 104A-C by processing the corresponding images 100A-C using a thresholding algorithm. The thresholding algorithm assigns each pixel to white or black, depending on whether a brightness level of the pixel exceeds a threshold brightness level.

Image 100A corresponds to a wheel 4 (FIG. 7) having cold brakes, image 100B corresponds to a wheel 4 having warm brakes, and image 100C corresponds to a wheel 4 having hot bearings. As can be seen, the infrared data 102A-C generated by applying an edge detection algorithm yields a clear distinction between cold brakes infrared data 102A and warm brakes infrared data 102B. However, only a minimal difference is present between warm bearings infrared data 102C and the normal bearings of infrared data 102A-B. As a result, the edge detection algorithm may not efficiently detect warm bearings. Additionally, the infrared data 104A-C generated by applying a thresholding algorithm can be used to readily distinguish between both cold brakes (infrared data 104A) and warm brakes (infrared data 104B) and hot bearings (infrared data 104C) and normal bearings (infrared data 104A-B).

It is understood that each algorithm can be calibrated to successfully evaluate infrared images 100A-C. For example, the thresholding algorithm can be calibrated so that the threshold brightness level is set to an expected brightness, which is based on a level of brightness that corresponds to proper braking and/or bearing operation. The thresholding algorithm can be executed multiple times, each with an expected brightness that corresponds to an anomaly. For example, a first expected brightness may be set to a highest acceptable brightness, above which the brake is labeled as "hot"; a second expected brightness may be set to a lowest acceptable brightness, below which the brake is labeled as "cold"; and a third expected brightness may be set to a highest acceptable brightness, above which the bearings are labeled as "hot". After each application of the thresholding algorithm, the resulting infrared data can be analyzed using any solution. The expected brightness may be adjusted based on one or more factors, such as ambient conditions, a weight of the vehicle, a typical amount of recent braking, and/or the like.

Returning to FIG. 2, it is understood that the edge detection and thresholding algorithms are only illustrative of various types and/or combinations of algorithms that analysis module 36 can implement. For example, with proper calibration, analysis module 36 can perform a thermal mapping of infrared images 100A-C (FIG. 8) and compare the actual heat values with expected values across different areas of a wheel 4 (FIG. 7) and/or vehicle 2 (FIG. 7). Further, analysis module 36 can process an infrared image of tread surface 8A (FIG. 7) to measure a depth of the tread, in which a temperature difference between high and low points depends on a thickness of the tread (e.g., a thicker tread will have a greater difference than a thinner tread). Still further, analysis module 36 can implement a curve-fitting algorithm to match edge features detected by the edge detection algorithm to a circle matching an expected area for detecting a brake cylinder. Still further, analysis module 36 can implement algorithms such as contrast enhancement, image histogram adjustment, blob and object detection, and/or the like. Additionally, evaluation data 50 can include other types of data for which analysis module 36 can implement similar algorithms for detecting relevant signal features in the data and discriminating between the absence or presence of one or more anomalies.

Figure 9:
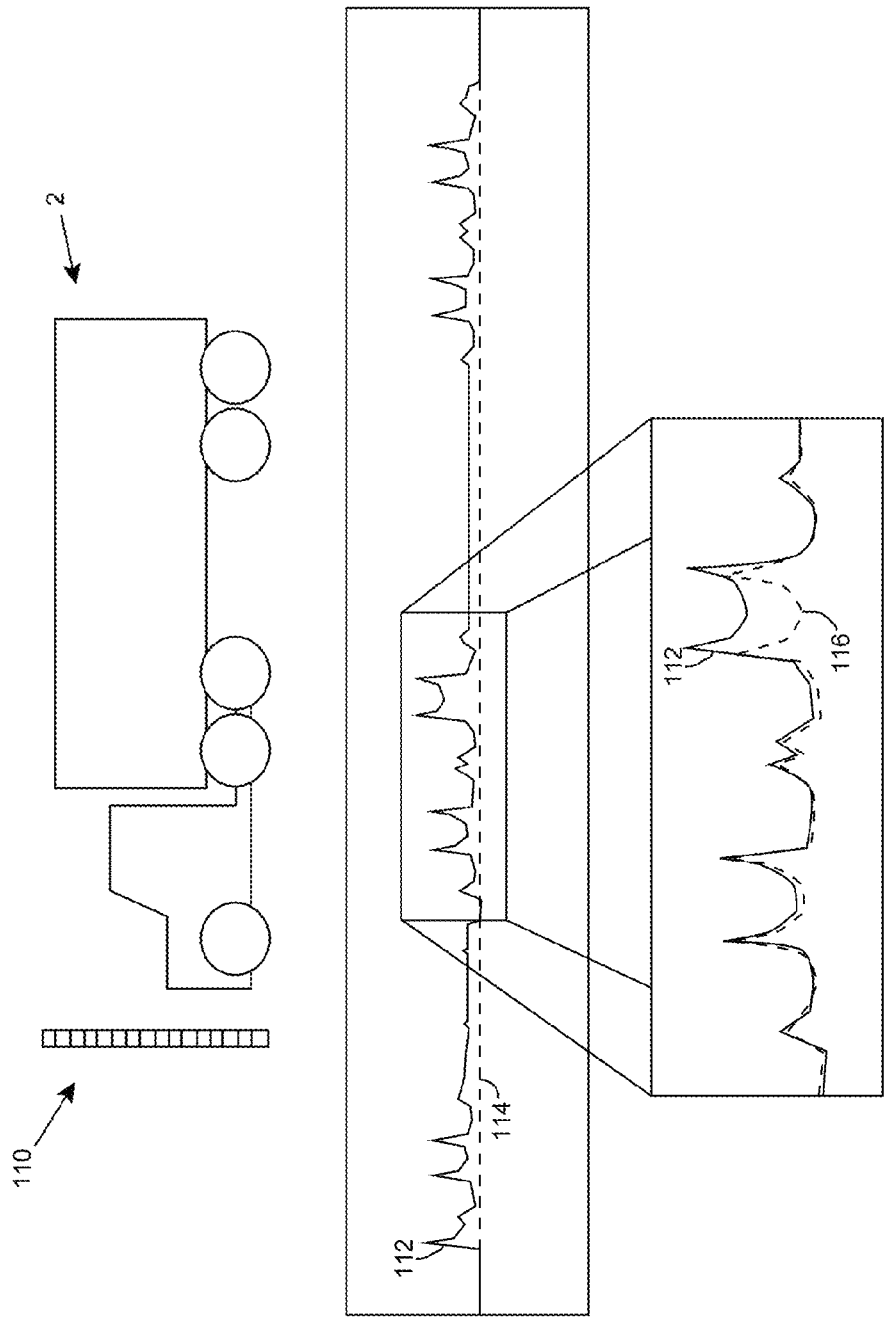
FIG. 9 shows an illustrative use of a linear array according to an embodiment.

In an embodiment, acquisition subsystem 12 detects a set of infrared signatures for vehicle 2 (FIG. 1). For example, acquisition subsystem 12 can include a linear array of infrared sensing devices that capture infrared data. FIG. 9 shows an illustrative use of a linear array 110 according to an embodiment. In general, vehicle 2 can pass linear array 110, which includes a plurality of infrared-sensing elements at varying heights. The data obtained by the infrared-sensing elements can be used to produce a set of infrared signatures 112 for vehicle 2 (e.g., by averaging or otherwise combining all the data, generating infrared signatures for multiple heights—wheel centerline, undercarriage height, etc.). The infrared signature(s) 112 can be normalized against an ambient temperature plot 114 can compared to an expected signature 116. A significant variation (e.g., based on a max/min temperature in infrared signature 112, a goodness of fit to expected signature 116, and/or the like) of infrared signature 112 from the expected signature 116 can identify a potential anomaly and/or be flagged for further inspection. For example, the variation shown in FIG. 9 may indicate that middle wheel of vehicle 2 is overheating. Further, it is understood that linear array 110 can be used to acquire image(s) of vehicle 2 by, for example, passively scanning vehicle 2 (e.g., imaging vehicle 2 in discrete sections as it passes), actively scanning vehicle 2 (e.g., using a mechanism to cause a field of view of linear array 110 to sweep a length of vehicle 2), and/or the like. These images can be used in the same manner as discussed herein.

The management (e.g., selection, calibration, utilization, etc.) of a set of algorithms for evaluating a vehicle 2 (FIG. 7) can be implemented using any type of artificial intelligence solution. For example, analysis module 36 can implement an expert system that comprises a set of condition examinations and corresponding action events, to evaluate vehicle 2. Such an expert system could include a condition examination such as a number of white pixels in infrared data 104A-C (FIG. 8), and perform some action (e.g., further analyze evaluation data 50 for hot/cold brakes, worn bearings, and/or the like) if the number is below/above an expected range. It is understood that the expert system can implement fuzzy logic (e.g., assign probabilities) to arrive at a conclusion with respect to the presence/absence of an anomaly in vehicle 2. Further, analysis module 36 can implement a neural network, which includes a series of connected neural units, each of which triggers upon a certain set of conditions. The neural network can be trained using sample data and include an ability to self-modify the characteristics of the units in the neural network using backpropagation or the like. Still further, analysis module 36 can implement template or pattern matching, in which evaluation data 50 is compared to a set of templates or patterns that have particular characteristics of interest. In this case, a proper tolerance for assigning matches is critical so that evaluation data 50 is not under or over matched with the corresponding templates or patterns.

As discussed herein, evaluation data 50 can include multiple types of data on vehicle 2 (FIG. 1), which can be obtained at varying locations and/or times, and which have been fused by processing module 34. In this case, analysis module 36 can compare features detected in the different types of data, and eliminate some potential confounding variables that can yield a false positive/negative. For example, holes 6C (FIG. 7) may be visible in a visible image and only visible in infrared data if an anomaly is present. When visible in the infrared data, analysis module 36 can overlay the locations with the visible image to verify a location of the hot spots. Additionally, acoustic data can be used to determine whether a sound typically associated with a failing bearing is present when a bearing-related anomaly is indicated by infrared data. Still further, visible light and infrared-based profiles of vehicle 2 can be compared to determine the location of infrared heat signatures as compared with known vehicular systems.

To assist in calibrating computer system 11, an infrared calibration fixture can be obtained, which includes a thermal grid pattern tailored for use in calibrating computer system 11 using any solution. An infrared device, such as infrared devices 12A-B (FIG. 1), can include an automatic internal shutter that provides relative zeroing capability. For example, the internal shutter can provide an imager with an effectively even temperature at all points for calibration between pixels. To this extent, infrared arrays can include pixels of different specific reactivity, sensitivity, and gain, which must be calibrated to produce an accurate and even image.

Additionally, it may be desirable to determine an approximate temperature of objects/features detected in an infrared image. To this extent, a target (such as the infrared calibration fixture) having areas of known temperatures (within a tolerance) can be placed in the field of view of an infrared device 12A-B (FIG. 1) during imaging of vehicle 2 (FIG. 1). In this case, the imaged target can be compared with the infrared image of vehicle 2 to determine a temperature corresponding to the objects/features detected on vehicle 2. The target can be constructed using heating/cooling elements and thermostatic elements that ensure that the temperature of the components is maintained to within relatively small tolerances. Additionally, the target can be customized to fit appropriate infrared emissivity profiles of one or more components, e.g., of braking components, thereby providing similar patterns that would be seen from the corresponding component(s).

Further, the fields of view for two or more infrared devices 12A-B can be registered with one another so that the locations of common elements can be accurately determined. A bandpass filter or the like can be used to adjust a temperature sensing range for of one or more of the infrared devices 12A-B to a slightly different band. Differences in the images captured by the infrared devices 12A-B would then be due to differences in the heat radiation emitted. These differences can be used to generate a temperature map for vehicle 2. Alternatively, a single infrared device 12A-B with switchable and/or tunable filters may be used.

An inherent temperature sensing range for many infrared devices 12A-B may be narrower than that of a range of temperatures of potential interest. For example, many commercial infrared devices 12A-B "top out" at around 500 degrees Fahrenheit, while exhaust gases, highly heated components of exhaust systems, failing brakes/bearing, and/or the like, may have temperatures around 1,000 degrees Fahrenheit. To this extent, acquisition subsystem 12 can include one or more components to detect temperature variations across wider ranges of temperatures. In an embodiment, acquisition subsystem 12 uses a neutral-density filter to effectively reduce the radiation by a factor (e.g., 3:1, 10:1, and/or the like) across the sensitive band of infrared devices 12A-B. In this case, saturation will not occur until a much higher temperature, but some sensitivity will be lost. For example, using a factor of 3:1 will result in a 1500 degree span being imaged across a 500 degree span.

Additionally, acquisition subsystem 12 can fuse multiple captured frames having different characteristics (e.g., longer exposure, different filters, and/or the like) into a higher-bit resolution digital image that maintains the temperature information in each separate frame. For example, three frames, each of which has a 300 degree sensitive range in three adjacent ranges (e.g., 0-300, 300-600, 600-900) can be utilized. The frames can be superimposed with sufficient color and brightness bit resolution to discriminate clearly between all three conditions throughout the fused frame. When performed on a moving target, such as vehicle 2 (FIG. 1), acquisition subsystem 12 must register the images across the frames, compensate for the movement, potential blurring, and/or the like, and combine the images into a single registered composite image for analysis.

Computer system 11 is described herein as performing a preliminary evaluation of vehicles, and providing some or all of evaluation data 50 for use by an inspection system 40. A particular embodiment would include implementation of computer system 11 as part of a commercial vehicle inspection station (e.g., weigh station). In this manner, individuals using the inspection system 40 can use the data to perform a more focused inspection of a particular vehicle and/or set of vehicles, while allowing vehicles without any detected anomalies to proceed more quickly through the inspection. As a result, inspection system 40 can more efficiently inspect vehicles while removing a higher percentage of unsafe vehicles from operation.

However, it is understood that this embodiment is only illustrative. For example, computer system 11 can be implemented as part of a fleet management system for a fleet of vehicles, such as commercial vehicles or buses. In this case, computer system 11 can obtain a historical record of previous inspection(s) and can permit condition-based rather than schedule-based maintenance on the vehicles. As a result, a fleet owner will only need to replace parts that are actually out of a given tolerance range, saving the expense of replacing parts too early. Such an embodiment can evaluate vehicles as they arrive and/or depart to/from a destination (e.g., a warehouse). Additionally, a third party maintenance company could charge the fleet owner only for those vehicles/components that are found out of tolerance. Further, computer system 11 can be integrated into other types of operations, such as security applications, manufacturer databases, governmental regulation compliance systems, and/or the like.

Further, while aspects of the invention have been shown and described with respect to the use of infrared data with or without other types of data in evaluating a vehicle, it is understood that alternative embodiments may be implemented without the use of infrared data. To this extent, embodiments may obtain evaluation data that includes image data based on visible light, ultraviolet light, and/or the like and/or non-image data, such as radar data, X-ray data, radiation data, magnetic data, pressure data, spectrometric data, acoustic data, a weight, and/or the like. The particular combination of types of data can be varied based on a particular application of the embodiment. For example, an embodiment can obtain ultraviolet light-based image data that is used to evaluate a presence of an unacceptable amount of strain for one or more parts of the vehicle. Additionally, an embodiment can obtain acoustic data, which can be evaluated to determine engine performance, bearing performance, and/or the like.

While shown and described herein as a method and system for evaluating a vehicle, it is understood that the invention further provides various alternative embodiments. For example, in one embodiment, the invention provides a computer program stored on a computer-readable medium, which when executed, enables a computer system to evaluate a vehicle. To this extent, the computer-readable medium includes program code, such as evaluation program 30 (FIG. 2), which implements the process described herein. It is understood that the term "computer-readable medium" comprises one or more of any type of tangible medium of expression capable of embodying a copy of the program code (e.g., a physical embodiment). In particular, the computer-readable medium can comprise program code embodied on one or more portable storage articles of manufacture, on one or more data storage portions of a computing device, such as storage component 24 (FIG. 2), as a data signal traveling over a network (e.g., during a wired/wireless electronic distribution of the computer program), on paper (e.g., capable of being scanned and converted to electronic data), and/or the like.

In another embodiment, the invention provides a method of generating a system for evaluating a vehicle. In this case, a computer system, such as computer system 11 (FIG. 1), can be obtained (e.g., created, maintained, having made available to, etc.) and one or more programs/systems for performing the process described herein can be obtained (e.g., created, purchased, used, modified, etc.) and deployed to the computer system. To this extent, the deployment can comprise one or more of: (1) installing program code on a computing device, such as computing device 20 (FIG. 2), from a computer-readable medium; (2) adding one or more computing devices to the computer system; and (3) incorporating and/or modifying one or more existing devices of the computer system, to enable the computer system to perform the process described herein.

In still another embodiment, the invention provides a business method that performs the process described herein on a subscription, advertising, and/or fee basis. That is, a service provider could offer to evaluate one or more vehicles as described herein. In this case, the service provider can manage (e.g., create, maintain, support, etc.) a computer system, such as computer system 11 (FIG. 1), that performs the process described herein for one or more customers. In return, the service provider can receive payment from the customer(s) under a subscription and/or fee agreement, receive payment from the sale of advertising to one or more third parties, and/or the like.

As used herein, it is understood that "program code" means any set of statements or instructions, in any language, code or notation, that cause a computing device having an information processing capability to perform a particular function either directly or after any combination of the following: (a) conversion to another language, code or notation; (b) reproduction in a different material form; and/or (c) decompression. To this extent, program code can be embodied as any combination of one or more types of computer programs, such as an application/software program, component software/a library of functions, an operating system, a basic I/O system/driver for a particular computing, storage and/or I/O device, and the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A method of evaluating a vehicle, the method comprising:
processing infrared data corresponding to at least one side of the vehicle acquired in a single pass of the vehicle using a computer system including at least one computing device to enhance a set of signal features in the infrared data and extract infrared wheel data corresponding to each of a plurality of wheels on the vehicle from the infrared data, wherein the processing uses at least one enhancement process selected from a group of enhancement processes based on at least one anomaly, the group of enhancement processes including: segmentation, fusion of multiple infrared images in the infrared data, edge detection within an infrared image in the infrared data, applying thresholding to assign a pixel in the infrared data to white or black, and feature detection of a wheel of the vehicle in the infrared data; and
analyzing the infrared data to determine a presence of at least one anomaly; and
providing a result of the analyzing for use by an inspection station.

2. The method of claim 1, further comprising:
automatically detecting a presence of the vehicle; and
automatically obtaining evaluation data in response to the detected presence.

3. The method of claim 2, the obtaining evaluation data including obtaining visible image data of the vehicle, and the method further comprising analyzing the visible image data.

4. The method of claim 2, the obtaining evaluation data including:
acquiring a first infrared image for a first side of the vehicle; and
acquiring a second infrared image for a second side of the vehicle.

5. The method of claim 4, the analyzing including examining a portion of each of the first and second infrared images that includes at least one of: a wheel or a brake of the vehicle.

6. The method of claim 5, the examining including comparing a brightness of a portion of the at least one of: the wheel or the brake with an expected brightness.

7. The method of claim 6, the portion of the wheel comprising at least one of:
a wheel rim or a tread surface.

8. The method of claim 4, wherein at least one of the acquirings uses an infrared imaging device located below the vehicle.

9. A system comprising:
a computer system configured to evaluate a vehicle, the computer system including at least one computing device for performing a method comprising:
processing infrared data corresponding to at least one side of the vehicle acquired in a single pass of the vehicle using a computer system including at least one computing device to enhance a set of signal features in the infrared data and extract infrared wheel data corresponding to each of a plurality of wheels on the vehicle from the infrared data, wherein the processing uses at least one enhancement process selected from a group of enhancement processes based on at least one anomaly, the group of enhancement processes including: segmentation, fusion of multiple infrared images in the infrared data, edge detection within an infrared image in the infrared data, applying thresholding to assign a pixel in the infrared data to white or black, and feature detection of a wheel of the vehicle in the infrared data; and
analyzing the infrared data to determine a presence of at least one anomaly; and
providing a result of the analyzing for use by an inspection station.

10. The system of claim 9, the method further comprising:
automatically detecting a presence of the vehicle; and
automatically obtaining evaluation data in response to the detected presence.

11. The system of claim 9, the method further comprising analyzing visible image data corresponding to the vehicle.

12. The system of claim 9, further comprising an acquisition component located in a path of the vehicle.

13. The system of claim 12, wherein the acquisition component includes a set of infrared imaging devices configured to acquire the infrared data while located below the vehicle.

14. The system of claim 13, wherein the set of infrared imaging devices includes a single infrared imaging device configured to acquire infrared image data for both a first side of the vehicle and for a second side of the vehicle opposite the first side of the vehicle.

15. The system of claim 9, the at least one anomaly including at least one of:
a brake anomaly, a bearing anomaly, or a wheel anomaly.

16. A system comprising:
an acquisition component located in a path of a vehicle to be evaluated, wherein the acquisition component includes a set of infrared imaging devices configured to acquire infrared data while located below the vehicle during a single pass of the vehicle; and
a computer system configured to evaluate the vehicle, the computer system including at least one computing device for performing a method comprising:
processing the infrared data to enhance a set of signal features in the infrared data and extract infrared wheel data corresponding to each of a plurality of wheels on the vehicle from the infrared data, wherein the processing uses at least one enhancement process selected from a group of enhancement processes based on at least one anomaly, the group of enhancement processes including: segmentation, fusion of multiple infrared images in the infrared data, edge detection within an infrared image in the infrared data, applying thresholding to assign a pixel in the infrared data to white or black, and feature detection of a wheel of the vehicle in the infrared data.

17. The system of claim 16, wherein the set of infrared imaging devices includes a single infrared imaging device configured to acquire infrared image data for both a first side of the vehicle and for a second side of the vehicle opposite the first side of the vehicle.

18. The system of claim 16, the method further comprising:
analyzing the infrared data to determine a presence of at least one anomaly; and
providing a result of the analyzing for use by an inspection station.

19. The system of claim 18, the at least one anomaly including at least one of:
a brake anomaly, a bearing anomaly, or a wheel anomaly.

20. The system of claim 16, further comprising a system for obtaining non-infrared data for the vehicle during the single pass of the vehicle.

* * * * *